(12) United States Patent
Dobbs et al.

(10) Patent No.: US 7,320,833 B2
(45) Date of Patent: Jan. 22, 2008

(54) ELECTROLUMINESCENT PLATINUM COMPOUNDS AND DEVICES MADE WITH SUCH COMPOUNDS

(75) Inventors: Kerwin D. Dobbs, Wilmington, DE (US); Norman Herron, Newark, DE (US); Viacheslav A. Petrov, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 374 days.

(21) Appl. No.: 10/774,285

(22) Filed: Feb. 6, 2004

(65) Prior Publication Data

US 2004/0197602 A1    Oct. 7, 2004

Related U.S. Application Data

(63) Continuation-in-part of application No. 10/768,209, filed on Jan. 30, 2004, now abandoned, and a continuation-in-part of application No. 10/284,728, filed on Oct. 31, 2002, now Pat. No. 7,166,368.

(60) Provisional application No. 60/347,910, filed on Nov. 7, 2001.

(51) Int. Cl.
*H01L 51/00* (2006.01)
*C07D 213/02* (2006.01)
*H01L 51/54* (2006.01)
*C09K 11/06* (2006.01)

(52) U.S. Cl. .................... 428/690; 428/917; 313/504; 257/E51.044; 546/4

(58) Field of Classification Search .............. 546/4
See application file for complete search history.

(56) References Cited

U.S. PATENT DOCUMENTS

| | | | |
|---|---|---|---|
| 5,552,678 A | 9/1996 | Tang et al. | |
| 6,303,238 B1 | 10/2001 | Thompson et al. | |
| 6,670,645 B2 | 12/2003 | Grushin et al. | |
| 6,911,271 B1 * | 6/2005 | Lamansky et al. | 428/690 |
| 6,916,554 B2 * | 7/2005 | Ma et al. | 428/690 |
| 6,953,628 B2 * | 10/2005 | Kamatani et al. | 428/690 |
| 7,011,897 B2 * | 3/2006 | Thompson et al. | 428/690 |
| 2001/0019782 A1 | 9/2001 | Igarashi et al. | |
| 2001/0053462 A1 | 12/2001 | Mishima | |
| 2002/0182441 A1 | 12/2002 | Lamansky et al. | |
| 2003/0108771 A1 | 6/2003 | Lecloux et al. | |
| 2003/0124381 A1 | 7/2003 | Thompson et al. | |
| 2004/0197602 A1 | 10/2004 | Dobbs et al. | |

FOREIGN PATENT DOCUMENTS

| | | |
|---|---|---|
| EP | 1 175 128 A2 | 1/2002 |
| EP | 1 191 614 A2 | 3/2002 |
| WO | WO 96/03410 A1 | 2/1996 |
| WO | WO 00/57676 A1 | 9/2000 |
| WO | WO 00/70655 A2 | 11/2000 |
| WO | WO 01/41512 A1 | 6/2001 |
| WO | WO 02/02714 A2 | 1/2002 |
| WO | WO 02/15645 A1 | 2/2002 |
| WO | WO 02/44189 A1 | 6/2002 |

OTHER PUBLICATIONS

Djurovich, Peter I. et al., Ir(III) Cyclometalated Complexes As Efficient Phosphorescent Emitters in Polymer Blend and Organic LEDs, Polymer Preprints, 2000, 770-771, 41(1).
Chatani, Naoto et al., Ru3(CO)12-Catalyzed Reaction of Pyridylbenzenes with Carbon Monoxide and Olefins. Carbonylation at a C-H Bond in the Benzene Ring, J. Org. Chem., 1997, 2604-2610, 62, American Chemical Society.
Gosmini, Corinne et al., Electrosynthesis of functionalized 2-arylpyridines from functionalized aryl and pyridine halides catalyzed by nickel bromide 2,2'-bipyridine complex, Tetrahedron Letters, 2000, 5039-5042, 41, Elsevier Science Ltd.
Cacchi, Sandro et al., The Palladium-Catalyzed Transfer Hydrogenation/Heterocyclization of B-(2-Aminophenyl-a,B-ynones. An Approach to 2-Aryl- and 2-Vinylquinolines, Synlett, 1999, 401-404, No. 4, Thieme Stuttgart, New York.
Baldo, M. A. et al., Very high-efficiency green organic light-emitting devices based on electrophosphorescence, Applied Physics Letters, Jul. 5, 1999, 4-6, 75(1) American Institue of Physics.
Baldo, M. A. et al., High-efficiency fluorescent organic light-emitting devices using a phosphorescent sensitizer, Nature, Feb. 17, 2000, 750-753, 403, Macmillan Magazines Ltd.
Wang, Yue et al., (Hydroxyphenyl)pyridine derivative, its metal complexes and application as electroluminescence material, Chemical Abstracts Service, Mar. 1, 2000, Database No. 133:315395.
Dedeian,K. et al., A New Synthetic Route to the Preparation of a Series of Strong Photoreducing Agents: fac Tris-Ortho-Metalated Complexes of Iridium(III) with Substituted 2-Phenylpyridines, Inorg. Chem., 1991, 1685-1687, 30(8), American Chemical Society.
Lamansky, Sergey et al., Highly Phosphorescent Bis-Cyclometalated Iridium Complexes: Synthesis, Photophysical Characterization, and Use in Organic Light Emitting Devices, J. Am. Chem. Soc., 2001, 4304-4312, 123, American Chemical Society.
Lamansky, Sergey et al., Synthesis and Characterization of Phosphorescent Cyclometalated Iridium Complexes, J. Am. Chem. Soc., 2001, 1704-1711, 40, American Chemical Society.
Lamansky, Sergey et al., Molecularly doped polymer light emitting diodes utilizing phosphorescent Pt(II) and Ir (III) dopants, Organic Electronics, 2001, 53-62, 2, Elsevier Science B.V.

* cited by examiner

*Primary Examiner*—Marie Yamnitzky
(74) *Attorney, Agent, or Firm*—John H. Lamming (57) ABSTRACT

The present invention is generally directed to electroluminescent Pt(II) complexes which have emission maxima across the visible spectrum, and devices that are made with the Pt(II) complexes.

17 Claims, 1 Drawing Sheet

FIG. 1

ELECTROLUMINESCENT PLATINUM COMPOUNDS AND DEVICES MADE WITH SUCH COMPOUNDS

CROSS REFERENCE TO RELATED APPLICATIONS

This application is a Continuation-In-Part of U.S. Ser. No. 10/768,209, filed Jan. 30, 2004, now abandoned, and a Continuation-In-Part of U.S. Ser. No. 10/284,728, filed Oct. 31, 2002 now U.S. Pat. No. 7,166,368, which claims priority to Provisional Application Ser. No. 60/347,910, dated Nov. 7, 2001.

BACKGROUND OF THE INVENTION

1. Field of the Invention

This invention relates to electroluminescent complexes of platinum(II). It also relates to electronic devices in which the active layer includes an electroluminescent Pt(II) complex.

2. Description of the Related Art

Organic electronic devices that emit light, such as light-emitting diodes that make up displays, are present in many different kinds of electronic equipment. In all such devices, an organic light-emitting layer is sandwiched between two electrical contact layers. At least one of the electrical contact layers is light-transmitting so that light can pass through the electrical contact layer. The organic layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, Friend et al., U.S. Pat. No. 5,247,190, Heeger et al., U.S. Pat. No. 5,408,109, and Nakano et al., Published European Patent Application 443 861. Complexes of 8-hydroxyquinolate with trivalent metal ions, particularly aluminum, have been extensively used as electroluminescent components, as has been disclosed in, for example, Tang et al., U.S. Pat. No. 5,552,678.

Electroluminescent devices with an light-emitting layer of polymer doped with organometallic complexes of platinum have been disclosed by Burrows and Thompson in published PCT application WO 00/57676. Electroluminescent complexes of platinum and electronic devices made with them have been disclosed by LeCloux et al. in published PCT application WO 03/040257.

However, there is a continuing need for efficient electroluminescent compounds.

SUMMARY OF THE INVENTION

The present invention is directed to a metal complex having Formula I, Formula II, or Formula III:

where:
in Formulae I, II, and III:
$L^1$ has Formula IV:

wherein:
$R^1$=H, $R^4$, $OR^4$, $N(R^4)_2$
$R^2$=H, $C_nF_{2n+1}$, $C_nF_{2n+1}SO_2$, $COOR^4$, CN
$R^3$=H, $C_nF_{2n+1}$, $C_nF_{2n+1}SO_2$, $COOR^4$, CN,
$R^4$ is the same or different at each occurrence and is H, alkyl, aryl, or adjacent $R^4$ groups can join together to form a 5- or 6-membered ring, and
n is an integer from 1 through 20;
in Formula II:
$L^2$ is a monoanionic bidentate ligand;
in Formula III:
$L^3$ is a monoanionic monodentate ligand; and
$L^4$ is a nonionic monodentate ligand.

In another embodiment, the present invention is directed to an organic electronic device having at least one active layer comprising the above metal complex, or combinations of the above metal complexes.

DETAILED DESCRIPTION OF THE PREFERRED EMBODIMENTS

The metal complexes of the invention have Formula I, Formula II, or Formula III, given above, and are referred to as cyclometallated complexes. The platinum is in the +2 oxidation state and is tetracoordinate. The complex in Formula I is a bis-cyclometallated complex. The complex in Formula II is a cyclometallated complex with an additional monoanionic bidentate ligand, $L^2$. The complex in Formula III is a cyclometallated complex with two additional monodentate ligands, $L^3$ and $L^4$. The cyclometallated complexes are neutral and non-ionic, and can be sublimed intact. Thin films of these materials obtained via vacuum deposition may exhibit good to excellent electroluminescent properties.

Ligand $L^1$ having Formula IV, shown above, is derived from a phenyl-pyridine parent compound. In one embodiment of Formula IV, $R^2$ and $R^3$ are independently selected from H, $CF_3$, $C_2F_5$, n-$C_3F_7$, i-$C_3F_7$, $C_4F_9$, $CF_3SO_2$, $COOR^{14}$ and CN.

The parent ligand compounds, $HL^1$, can generally be prepared by standard palladium-catalyzed Suzuki or Kumada cross-coupling of the corresponding heterocyclic aryl chloride with an organoboronic acid or organomagnesium reagent, as described in, for example, O. Lohse, P.

Thevenin, E. Waldvogel *Synlett*, 1999, 45-48. This reaction is illustrated in Equation (1) below.

In one embodiment, ligand $L^1$ is selected from the following ligands in Table 1 below.

TABLE 1

| Ligands Having Formula IV | | | |
|---|---|---|---|
| Ligand | $R^1$ | $R^2$ | $R^3$ |
| 1-a | H | H | H |
| 1-b | H | $CF_3$ | H |
| 1-c | H | COOMe | H |
| 1-d | H | CN | H |
| 1-e | $CH_3$ | H | H |
| 1-f | $CH_3$ | $CF_3$ | H |
| 1-g | $CH_3$ | COOMe | H |
| 1-h | $CH_3$ | CN | H |
| 1-i | $CH_3$ | H | H |
| 1-j | t-butyl | H | H |
| 1-k | OMe | $CF_3$ | H |
| 1-l | OMe | COOMe | H |
| 1-m | OMe | CN | H |
| 1-n | OMe | $CF_3$ | $CF_3$ |
| 1-o | $NMe_2$ | H | H |
| 1-p | $NMe_2$ | $CF_3$ | H |
| 1-q | $NMe_2$ | COOMe | H |
| 1-r | $NMe_2$ | CN | H |
| 1-s | $NMe_2$ | $CF_3SO_2$ | H |
| 1-t | $NMe_2$ | $C_2F_5$ | H |
| 1-u | $NMe_2$ | $CF(CF_3)_2$ | H |
| 1-v | $NMe_2$ | H | H |
| 1-w | $NPh_2$ | $CF_3$ | H |
| 1-x | $NPh_2$ | COOMe | H |
| 1-y | $NPh_2$ | CN | H |

In one embodiment, ligand $L^1$ is derived from parent compounds having Formula V, Formula VI, Formula VII, Formula VIII, and Formula IX below:

(V)

(VI)

(VII)

(VIII)

(IX)

The $L^2$ ligand is a monoanionic bidentate ligand. In general these ligands have N, O, P, or S as coordinating atoms and form 5- or 6-membered rings when coordinated to the platinum. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and diarylphosphinoalkanols (diarylphosphinoalkoxide ligands). In one embodiment, $L^2$ is selected from a β-enolate and a phosphino alkoxide.

The β-enolate ligands generally have the Formula X (X)

where $R^5$ is the same or different at each occurrence. The $R^5$ groups can be hydrogen, halogen, substituted or unsubstituted alkyl, aryl, alkylaryl or heterocyclic groups. Adjacent $R^5$ and $R^6$ groups can be joined to form five- and sixmembered rings, which can be substituted. In one embodiment, $R^5$ groups are selected from $C_n(H+F)_{2n+1}$, —$C_6H_5$, c-$C_4H_3S$, and c-$C_4H_3O$, where n is an integer from 1 through 20. The $R^6$ group can H, be substituted or unsubstituted alkyl, aryl, alkylaryl or heterocyclic groups, or fluorine.

Examples of suitable β-enolate ligands include the compounds listed below. The abbreviation for the β-enolate form is given below in brackets.

2,4-pentanedionate [acac]
1,3-diphenyl-1,3-propanedionate [DI]
2,2,6,6-tetramethyl-3,5-heptanedionate [TMH]
4,4,4-trifluoro-1-(2-thienyl)-1,3-butanedionate [TTFA]
7,7-dimethyl-1,1,1,2,2,3,3-heptafluoro-4,6-octanedionate [FOD]
1,1,1,3,5,5,5-heptafluoro-2,4-pentanedionate [F7acac]
1,1,1,5,5,5-hexaflouro-2,4-pentanedionate [F6acac]
1-phenyl-3-methyl-4-i-butyryl-pyrazolinonate [FMBP]

The β-dicarbonyl parent compounds, are generally available commercially. The parent compound 1,1,1,3,5,5,5-heptafluoro-2,4-pentanedione, $CF_3C(O)CFHC(O)CF_3$, can be prepared using a two-step synthesis, based on the reaction of perfluoropentene-2 with ammonia, followed by a hydrolysis step. This compound should be stored and reacted under anhydrous conditions as it is susceptible to hydrolysis.

The hydroxyquinolinate ligands can be substituted with groups such as alkyl or alkoxy groups which may be partially or fully fluorinated. Examples of suitable hydroxyquinolinate ligands include (with abbreviation provided in brackets):

8-hydroxyquinolinate [8hq]
2-methyl-8-hydroxyquinolinate [Me-8hq]
10-hydroxybenzoquinolinate [10-hbq]

The parent hydroxyquinoline compounds are generally available commercially.

Phosphino alkoxide ligands generally have Formula XI, below:

(XI)

where
$R^7$ can be the same or different at each occurrence and is selected from H and $C_n(H+F)_{2n+1}$,
$R^8$ can be the same or different at each occurrence and is selected from $C_n(H+F)_{2n+1}$ and $C_6(H+F)_5$, or $C_6H_{5-b}(R^9)_b$,
$R^9$=$CF_3$, $C_2F_5$, n-$C_3F_7$, i-$C_3F_7$, $C_4F_9$, $CF_3SO_2$, and
φ is 2 or 3;
b is 0-5; and
n is 1-20.

Examples of suitable phosphino alkoxide ligands include (with abbreviation provided in brackets):

3-(diphenylphosphino)-1-oxypropane [dppO]
1,1-bis(trifluoromethyl)-2-(diphenylphosphino)-ethoxide [tfmdpeO]

Some of the parent phosphino alkanol compounds are available commercially, or can be prepared using known procedures, such as, for example, the procedure reported for ffmdpeO in *Inorg. Chem.* 1985, v.24, p.3680.

In one embodiment, the phosphino alkoxide has Formula XII below:

(XII)

In one embodiment, $L^2$ is a ligand coordinated through a carbon atom which is part of an aromatic group. The ligand can have Formula XIII:

(XIII)

wherein Ar is an aromatic group, Y is a group having a heteroatom capable of coordinating to Pt, q is 0 or an integer from 1 through 20, p is an integer from 1 through 5, and further wherein one or more of the carbons in $(CH_2)_q$ can be replaced with a heteroatom and one or more of the hydrogens in $(CH_2)_q$ can be replaced with D or F.

In one embodiment of Formula XIII, Y is selected from $N(R^{10})_2$, $OR^{10}$, $SR^{10}$, and $P(R^{11})_2$, wherein $R^{10}$ is the same or different at each occurrence and is H, $C_nH_{2n+1}$ or $C_n(H+F)_{2n+1}$ and $R^{11}$ is the same or different at each occurrence and is selected from H, $R^{10}$, Ar and substituted Ar.

In one embodiment of Formula XIII, Ar is phenyl, q is 1, Y is $P(Ar)_2$, and p is 1 or 2.

The $L^3$ ligand is a monoanionic monodentate ligand. Such ligands include, but are not limited to, $H^-$ ("hydride") and ligands having C, O or S as coordinating atoms. Coordinating groups include, but are not limited to alkoxide, carboxylate, thiocarboxylate, dithiocarboxylate, sulfonate, thiolate, carbamate, dithiocarbamate, thiocarbazone anions, sulfonamide anions, and the like. In some cases, ligands listed above as L', such as β-enolates and phosphinoakoxides, can act as monodentate ligands. The monodentate ligand can also be a coordinating anion such as halide, nitrate, sulfate, hexahaloantimonate, and the like. These ligands are generally available commercially.

The $L^4$ ligand is a nonionic monodentate ligand, such as CO or phosphine. In one embodiment, $L^4$ is a monodentate phosphine ligand having Formula XIV (XIV)

where Ar represents an aryl or heteroaryl group. The Ar group can be unsubstituted or substituted with alkyl, heteroalkyl, aryl, heteroaryl, halide, carboxyl, sulfoxyl, or amino groups. The $L^4$ phosphine ligands are generally available commercially.

In one embodiment, the complexes of the invention exhibit blue luminescence. In one embodiment, the complexes have photoluminescent and/or electroluminescent spectra which have a maximum at 500 nm or less. In one embodiment, the maximum is less than 480 nm.

Complexes of Formula I are generally prepared from metal chloride salts and an excess of the parent ligand compound $HL^1$. This is illustrated in Equation (2) below.

Complexes of Formula II are generally prepared from metal chloride salts by first forming the bridged chloride dimer. This reaction is illustrated in Equation (3) below.

Complexes of Formula II are then formed by adding a salt of the parent ligand compound, such as $NaL^2$, to the bridged chloride dimer. This reaction is illustrated using the sodium salt of a β-enolate ligand in Equation (4) below.

The salts of the parent ligand compounds can be made by any conventional methods, such as by the addition of sodium hydride to $HL^2$ in an inert solvent.

Complexes of Formula III are also generally prepared by first forming the bridged chloride dimer. To the dimer is then added the other two ligands. $L^3$ can be added as the silver salt, $AgL^3$. $L^4$ is added as the neutral ligand. The reaction is illustrated in Equation (5) below.

Electronic Device

Figure 1:
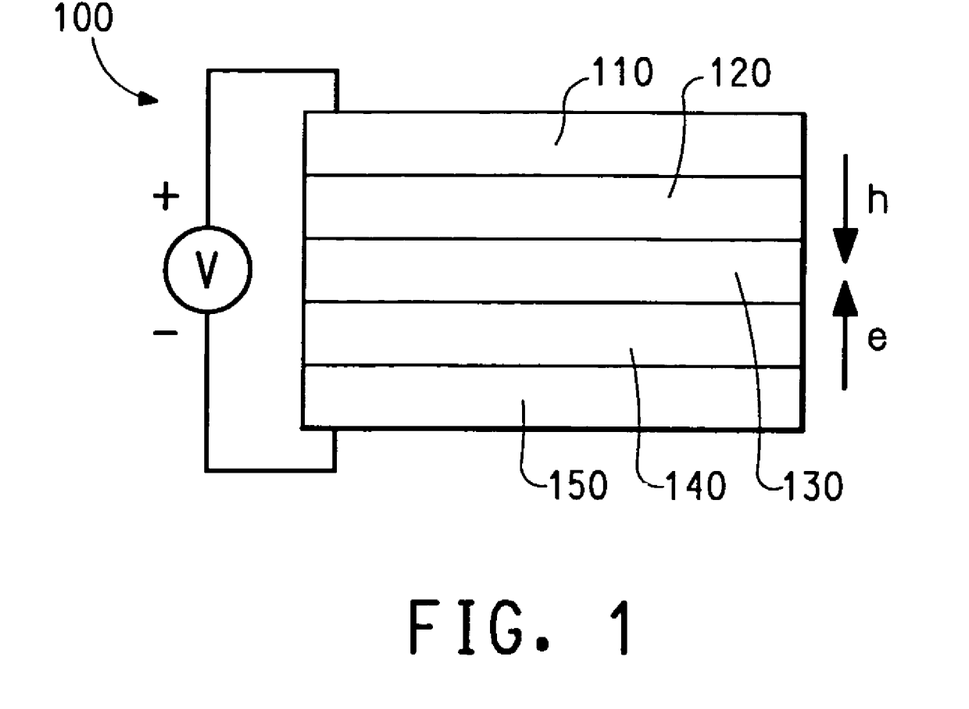
FIG. 1 is a schematic diagram of one example of a light-emitting device (LED).

The present invention also relates to an electronic device comprising at least one layer positioned between two electrical contact layers, wherein the at least one photoactive layer of the device includes the complex of the invention. FIG. 1 is an illustrative example of an organic electronic device comprising a photoactive layer that comprises the present invention. Other device architectures would benefit from the present invention, as well and are numerous. In FIG. 1, device 100 has an anode layer 110 and a cathode layer 150 and electroactive layers 120, 130 and optionally 140 between the anode 110 and cathode 150. Adjacent to the anode is a hole injection/transport layer 120. Adjacent to the cathode is an optional layer 140 comprising an electron transport material. Between the hole injection/transport layer 120 and the cathode (or optional electron transport layer) is the photoactive layer 130. Layers 120, 130, and 140 are individually and collectively referred to as the active layers.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary*, 470 and 476 (McGraw-Hill, Inc. 1966).

The complexes of the invention are particularly useful as the active material in the emitting layer of an OLED, or as electron transport material in layer 140. Preferably the platinum complexes of the invention are used as the light-emitting material in diodes. When used in layer 130, it has been found that the complexes of the invention do not need to be in a solid matrix diluent in order to be effective, althougth they may be. A layer that is greater than 20% by weight metal complex, based on the total weight of the layer, up to substantially 100% by weight metal complex, can be used as the emitting layer. By "substantially 100%" it is meant that the metal complex is the only material in the layer, with the possible exception of impurities or adventitious byproducts from the process to form the layer. Additional materials can be present in the emitting layer with the iridium compound. For example, a fluorescent dye may be present to alter the color of emission. A diluent may also be added and such diluent may be a charge transport material or an inert matrix. A diluent may comprise polymeric materials, small molecules or mixtures thereof. A diluent may act as a processing aid, may improve the physical or electrical properties of films containing the platinum compound, may decrease self-quenching in the platinum compounds, and/or may decrease the aggregation of the platinum compounds described herein. The diluent can comprise a polymeric material, small molecule or mixtures thereof. Non-limiting examples of such diluents include poly(N-vinyl carbazole) and polysilane. It can also be a small molecule, such as 4,4'-N,N'-dicarbazole biphenyl or tertiary aromatic amines. When a diluent is used, the metal complex is generally present in a small amount, usually less than 20% by weight, preferably less than 10% by weight, based on the total weight of the layer.

Examples of suitable conjugated polymers include polyarylenevinylenes, polyfluorenes, polyoxadiazoles, polyanilines, polythiophenes, polypyridines, polyphenylenes, copolymers thereof, and combinations thereof. The conjugated polymer can be a copolymer having non-conjugated portions of, for example, acrylic, methacrylic, or vinyl, monomeric units. In one embodiment, the diluent comprises homopolymers and copolymers of fluorene and substituted fluorenes.

In some cases the metal complexes of the invention may be present in more than one isomeric form, or mixtures of different complexes may be present. It will be understood that in the above discussion of OLEDs, the term "the metal complex" is intended to encompass mixtures of complexes and/or isomers.

The device generally also includes a support (not shown) which can be adjacent to the anode or the cathode. Most frequently, the support is adjacent the anode. The support can be flexible or rigid, organic or inorganic. Generally, glass or flexible organic films are used as a support. The anode 110 is an electrode that is particularly efficient for injecting or collecting positive charge carriers. The anode is preferably made of materials containing a metal, mixed metal, alloy, metal oxide or mixed-metal oxide. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymers," *Nature* vol. 357, pp 477-479 (11 Jun. 1992).

The anode layer 110 is usually applied by a physical vapor deposition process or spin-cast process. The term "physical vapor deposition" refers to various deposition approaches carried out in vacuo. Thus, for example, physical vapor deposition includes all forms of sputtering, including ion beam sputtering, as well as all forms of vapor deposition such as e-beam evaporation and resistance evaporation. A specific form of physical vapor deposition which is useful is rf magnetron sputtering.

There is generally a hole transport layer 120 adjacent the anode. Examples of hole transport materials for layer 120 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules, in addition to TPD and MPMP mentioned above, are: 1,1-bis[(di4-tolylamino) phenyl]cyclohexane (TAPC); N,N'-bis(4-methylphenyl)-N,N'-bis(4-ethylphenyl)-[1,1'-(3,3'-dimethyl)biphenyl]4,4'-diamine (ETPD); tetrakis-(3-methylphenyl)-N,N,N',N'-2,5-phenylenediamine (PDA); a-phenyl-4-N,N-diphenylaminostyrene (TPS); p-(diethylamino)benzaldehyde diphenylhydrazone (DEH); triphenylamine (TPA); 1-phenyl-3-[p-(diethylamino)styryl]-5-[p-(diethylamino)phenyl] pyrazoline (PPR or DEASP); 1,2-trans-bis(9H-carbazol-9-yl)cyclobutane (DCZB); N, N, N',N'-tetrakis(4-methylphenyl)-(1,1'-biphenyl)4,4'-diamine (TTB); and porphyrinic compounds, such as copper phthalocyanine. Commonly used hole transporting polymers are polyvinylcarbazole, (phenylmethyl)polysilane, poly(3,4-ethylendioxythiophene) (PEDOT), and polyaniline. It is also possible to obtain hole transporting polymers by doping hole transporting molecules such as those mentioned above into polymers such as polystyrene and polycarbonate.

Optional layer 140 can function both to facilitate electron transport, and also serve as a buffer layer or anti-quenching layer to prevent quenching reactions at layer interfaces. Preferably, this layer promotes electron mobility and reduces quenching reactions. Examples of electron transport materials for optional layer 140 include metal chelated oxinoid compounds, such as tris(8-hydroxyquinolato)aluminum ($Alq_3$); phenanthroline-based compounds, such as 2,9-dimethyl-4,7-diphenyl-1,10-phenanthroline (DDPA) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ).

The cathode 150 is an electrode that is particularly efficient for injecting or collecting electrons or negative charge carriers. The cathode can be any metal or nonmetal having a lower work function than the first electrical contact layer (in this case, an anode). Materials for the second electrical contact layer can be selected from alkali metals of Group 1 (e.g., Li, Cs), the Group 2 (alkaline earth) metals, the Group 12 metals, the lanthanides, and the actinides. Materials such as aluminum, indium, calcium, barium, samarium and magnesium, as well as combinations, can be used.

It is known to have other layers in organic electronic devices. For example, there can be a layer (not shown) between the conductive polymer layer 120 and the active layer 130 to facilitate positive charge transport and/or band-gap matching of the layers, or to function as a protective layer. Similarly, there can be additional layers (not shown) between the active layer 130 and the cathode layer 150 to facilitate negative charge transport and/or band-gap matching between the layers, or to function as a protective layer. Layers that are known in the art can be used. In addition, any of the above-described layers can be made of two or more layers. Alternatively, some or all of inorganic anode layer 110, the conductive polymer layer 120, the active layer 130, and cathode layer 150, may be surface treated to increase charge carrier transport efficiency. The choice of materials for each of the component layers is preferably determined by balancing the goals of providing a device with high device efficiency.

It is understood that each functional layer may be made up of more than one layer.

The device can be prepared by sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be coated from solutions or dispersions in suitable solvents, using any conventional coating technique. In general, the different layers will have the following range of thicknesses: anode 110, 500-5000 Å, preferably 1000-2000 Å; hole transport layer 120, 50-2500 Å, preferably 200-2000 Å; light-emitting layer 130, 10-1000 Å, preferably 100-800 Å; optional electron transport layer 140, 50-1000Å, preferably 100-800 Å; cathode 150, 200-10,000Å, preferably 300-5000 Å. The location of the electron-hole recombination zone in the device, and thus the emission spectrum of the device, is affected by the relative thickness of each layer. For examples, when an emitter, such as $Alq_3$ is used as the electron transport layer, the electron-hole recombination zone can be in the $Alq_3$ layer. The emission would then be that of $Alq_3$, and not the desired sharp lanthanide emission. Thus the thickness of the electron-transport layer must be chosen so that the electron-hole recombination zone is in the light-emitting layer. The desired ratio of layer thicknesses will depend on the exact nature of the materials used.

It is understood that the efficiency of the devices of the invention made with metal complexes, can be further improved by optimizing the other layers in the device. For example, more efficient cathodes such as Ca, Ba, Mg/Ag, or LiF/Al can be used. Shaped substrates and novel hole transport materials that result in a reduction in operating voltage or increase quantum efficiency are also applicable. Additional layers can also be added to tailor the energy levels of the various layers and facilitate electroluminescence.

The complexes of the invention often are phosphorescent and photoluminescent and may be useful in other applications. For example, the complexes may be used as oxygen sensitive indicators, as phosphorescent indicators in bioassays, and as catalysts.

As used herein, the term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic ion. The letter "L" when used to designate a ligand having a nominal (−1) charge, is considered to be derived from the neutral parent compound, "HL", by the loss of a hydrogen ion. The term "complex", when used as a noun, is intended to mean a compound having at least one metallic ion and at least one ligand. The term "β-dicarbonyl" is intended to mean a neutral compound in which two ketone groups are present, separated by a CHR group. The term "β-enolate" is intended to mean the anionic form of the β-dicarbonyl in which the H from the CHR group between the two carbonyl groups has been abstracted. The term "group" is intended to mean a part of a compound, such as a substituent in an organic compound or a ligand in a complex. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "photoactive" refers to any material that exhibits electroluminescence and/or photosensitivity. In addition, the IUPAC numbering system is used throughout, where the groups from the Periodic Table are numbered from left to right as 1 through 18 (CRC Handbook of Chemistry and Physics, 81$^{st}$ Edition, 2000). In the Formulae and Equations, the letters L, R and Y are used to designate atoms or groups which are defined within. All other letters are used to designate conventional atomic symbols. The term "(H+F)" is intended to mean all combinations of hydrogen and fluorine, including completely hydrogenated, partially fluorinated or perfluorinated substituents. By "emission maximum" is meant the wavelength, in nanometers, at which the maximum intensity of electroluminescence is obtained. Electroluminescence is generally measured in a diode structure, in which the material to be tested is sandwiched between two electrical contact layers and a voltage is applied. The light intensity and wavelength can be measured, for example, by a photodiode and a spectrograph, respectively.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

The following examples illustrate certain features and advantages of the present invention. They are intended to be illustrative of the invention, but not limiting. All percentages are mole percents, unless otherwise indicated.

Example 1

This example illustrates the preparation of parent ligand compound V.

Preparation of 2,4-difluoro-3-trifluoromethylbenzeboronic acid

To a solution of 2.4 g of 2,6-difluoro-trifluoromethylbenzene in the mixture of 25 ml of dry ether and 25 ml of dry THF 7 ml of solution 2M butyl lithium in pentane was added dropwise at −70° C. The reaction mixture was stirred 15 min at −70° C. and 2 g of trimethylborate was added. The reaction was allowed to warm up to 25° C. and was diluted with 200 ml of 10% hydrochloric acid and extracted with ether (2×50 ml). The combined organic layers were washed with water (2×100 ml), dried over $MgSO_4$ and solvent was remover under vacuum at 50° C. to leave 3.4 g of crude boronic acid (containing ~50% of THF), which was used for the next reaction without further purification. $^1H$ NMR ($CDCl_3$): 6.9 (2H, t), 7.9 (1H, q), 5.3 (2H, br s); $^{19}F$ NMR: −56.68 (3F, t), −106.0 (1F, m), −108.0 (1F, m).

Preparation of 2-(2,4-difluoro-3-trifluoromethylphenyl)-pyridine. Formula V.

To a solution of 10 g potassium carbonate in 100 ml of degassed water, the solution of 3.4 g 2,4-difluoro-3-trifluoromethylbenzeneboronic acid (50% purity, the rest THF) in 50 ml of monoglyme was added, followed by the addition of 3.5 g of 2-bromopyridine, 0.1 g of dicyclohexyl(biphenyl)phosphine, 0.05 g of palladium acetate. The reaction mixture was refluxed (90-95° C.) for 16 h. The reaction mixture was diluted with 500 ml of water, extracted with dichloromethane (3×50 ml), the organic layer was washed with water (1×300 ml), dried over $MgSO_4$ and solvent was removed under vacuum. Crude product (3.2 g) was dissolved in 50 ml of hexane and the solution was passed through a short plug of silicagel (Silicagel 60, EM Science). The column was washed with another 30 ml of hexane. From final solution hexane was removed under vacuum to leave 1.6 g of slightly yellow liquid, which based on NMR analysis was 2-(2,4-difluoro-3-trifluoromethylphenyl)-pyridine, containing 27% of 2-bromopyridine. The crude material was used for the next reaction without further purification.

Example 2

This example illustrates the preparation of a complex of the invention having Formula XV:

To 0.18 g platinum chloride and 0.1 g tetrapentylammonium chloride in 10 mL chlorobenzene was added 0.18 g of the parent ligand compound from Example 1. This was refluxed under nitrogen for 1 hour and then evaporated to dryness in a nitrogen stream. The residue was redissolved into 5 mL 2-ethoxyethanol to which was added 0.24 g di-t-butylacetylacetone (tetramethylheptanedione) and 180 mg sodium carbonate. This mixture was refluxed under nitrogen for 30 mins and then cooled. This was then evaporated to dryness in a nitrogen stream, extracted into methylene chloride, and filtered through silica to remove dark brown material. The solid was recrystallized from methanol/methylene chloride, resulting in a pale yellow solid which was bright blue green luminescent. Analysis by nmr indicated that the material had Formula XV.

What is claimed is:

1. An active layer comprising at least one compound having Formula III:

$$PtL^1L^3L^4 \quad (III)$$

where:

$L^1$ has Formula IV:

(IV)

wherein:

$R^1$=H, $R^4$, $OR^4$, $N(R^4)_2$
$R^2$=H, $C_nF_{2n+1}$,
$R^3$=H, $C_nF_{2n+1}$,
$R^4$ is the same or different at each occurrence and is H, alkyl, aryl, or adjacent $R^4$ groups can join together to form a 5- or 6-membered ring, and
n is an integer from 1 through 20;
$L^3$ is a monoanionic monodentate ligand; and
$L^4$ is a nonionic monodentate phosphine ligand.

2. The active layer of claim 1, wherein $R^2$ and $R^3$ are independently selected from H, $CF_3$, $C_2F_5$, n-$C_3F_7$, i-$C_3F_7$, and $C_4F_9$.

3. An organic electronic device comprising at least one active layer of claim 1.

4. An active layer of claim 1 further comprising a diluent.

5. An active layer of claim 4 wherein the diluent further comprises a material selected from a polymer, a small molecule, and a mixture thereof.

6. A compound having Formula III:

$$PtL^1L^3L^4 \quad (III)$$

where:

$L^1$ has Formula IV:

(IV)

wherein:

$R^1$=H, $R^4$, $OR^4$, $N(R^4)_2$
$R^2$=H, $C_nF_{2n+1}$,
$R^3$=H, $C_nF_{2n+1}$,
$R^4$ is the same or different at each occurrence and is H, alkyl, aryl, or adjacent $R^4$ groups can join together to form a 5- or 6-membered ring, and
n is an integer from 1 through 20;
$L^3$ is a monoanionic monodentate ligand; and
$L^4$ is a nonionic monodentate phosphine ligand.

7. A compound of claim 6, wherein $R^2$ and $R^3$ are independently selected from H, $CF_3$, $C_2F_5$, n-$C_3F_7$, i-$C_3F_7$, and $C_4F_9$.

8. An organic electronic device comprising a layer that comprises the compound of claim 6.

9. An active layer comprising at least one compound having Formula I $$Pt(L^1)_2 \quad (I)$$

wherein $L^1$ is selected from Formula VII and Formula VIII:

(VII)

(VIII)

10. A compound having Formula II:

$$PtL^1L^2 \quad (II)$$

where:

$L^1$ has Formula IV:

(IV)

wherein:

R¹=H, R⁴, OR⁴, N(R⁴)₂

R²=H, $C_nF_{2n+1}$, $C_nF_{2n+1}SO_2$, COOR⁴, CN

R³=H, $C_nF_{2n+1}$, $C_nF_{2n+1}SO_2$, COOR⁴, CN,

R⁴ is the same or different at each occurrence and is H, alkyl, aryl, or adjacent R⁴ groups can join together to form a 5- or 6-membered ring, and n is an integer from 1 through 20; and L² is a phosphino alkoxide.

11. The compound of claim 10, wherein L¹ is selected from ligands 1-a through 1-y:

| Ligand | R¹ | R² | R³ |
|---|---|---|---|
| 1-a | H | H | H |
| 1-b | H | CF₃ | H |
| 1-c | H | COOMe | H |
| 1-d | H | CN | H |
| 1-e | CH₃ | H | H |
| 1-f | CH₃ | CF₃ | H |
| 1-g | CH₃ | COOMe | H |
| 1-h | CH₃ | CN | H |
| 1-i | CH₃ | H | H |
| 1-j | t-butyl | H | H |
| 1-k | OMe | CF₃ | H |
| 1-l | OMe | COOMe | H |
| 1-m | OMe | CN | H |
| 1-n | OMe | CF₃ | CF₃ |
| 1-o | NMe₂ | H | H |
| 1-p | NMe₂ | CF₃ | H |
| 1-q | NMe₂ | COOMe | H |
| 1-r | NMe₂ | CN | H |
| 1-s | NMe₂ | CF₃SO₂ | H |
| 1-t | NMe₂ | C₂F₅ | H |
| 1-u | NMe₂ | CF(CF₃)₂ | H |
| 1-v | NMe₂ | H | H |
| 1-w | NPh₂ | CF₃ | H |
| 1-x | NPh₂ | COOMe | H |
| 1-y | NPh₂ | CN | H. |

12. An organic electronic device comprising a layer that comprises the compound of claim 11.

13. An organic electronic device comprising a layer that comprises the compound of claim 10.

14. An active layer comprising at least one compound having a formula selected from Formula II and Formula III:

$$PtL^1L^2 \quad (II)$$

$$PtL^1L^3L^4 \quad (III)$$

where:

in Formulae III and III:

L¹ is selected from Formula VII and Formula VIII:

(VII)

(VIII)

in Formula II:

L² is a phosphino alkoxide;

in Formula III:

L³ is a monoanionic monodentate ligand; and

L⁴ is a nonionic monodentate ligand.

15. An active layer comprising at least one compound having Formula II:

$$PtL^1L^2 \quad (II)$$

where:

L¹ has Formula IV:

(IV)

wherein:

R¹=H, R⁴, OR⁴, N(R⁴)₂

R²=H, $C_nF_{2n+1}$, $C_nF_{2n+1}SO_2$, COOR⁴, CN

R³=H, $C_nF_{2n+1}$, $C_nF_{2n+1}SO_2$, COOR⁴, CN

R⁴ is the same or different at each occurrence and is H, alkyl, aryl, or adjacent R⁴ groups can join together to form a 5- or 6-membered ring, and n is an integer from 1 through 20; and L² is a phosphino alkoxide.

16. The active layer of claim 15, wherein L¹ is selected from ligand 1-a through 1-y:

| Ligand | R¹ | R² | R³ |
|---|---|---|---|
| 1-a | H | H | H |
| 1-b | H | CF₃ | H |
| 1-c | H | COOMe | H |
| 1-d | H | CN | H |
| 1-e | CH₃ | H | H |
| 1-f | CH₃ | CF₃ | H |
| 1-g | CH₃ | COOMe | H |
| 1-h | CH₃ | CN | H |
| 1-i | CH₃ | H | H |
| 1-j | t-butyl | H | H |
| 1-k | OMe | CF₃ | H |
| 1-l | OMe | COOMe | H |
| 1-m | OMe | CN | H |

-continued

| Ligand | R¹ | R² | R³ |
|---|---|---|---|
| 1-n | OMe | CF₃ | CF₃ |
| 1-o | NMe₂ | H | H |
| 1-p | NMe₂ | CF₃ | H |
| 1-q | NMe₂ | COOMe | H |
| 1-r | NMe₂ | CN | H |
| 1-s | NMe₂ | CF₃SO₂ | H |
| 1-t | NMe₂ | C₂F₅ | H |
| 1-u | NMe₂ | CF(CF₃)₂ | H |
| 1-v | NMe₂ | H | H |
| 1-w | NPh₂ | CF₃ | H |
| 1-x | NPh₂ | COOMe | H |
| 1-y | NPh₂ | CN | H. |

17. The active layer of claim 15, wherein $L^1$ is selected from Formula V, Formula VI, Formula VII, Formula VIII, and Formula IX:

(V)

(VI)

(VII)

(VIII)

(IX)

* * * * *